US005881732A

United States Patent [19]
Sung et al.

[11] Patent Number: 5,881,732
[45] Date of Patent: *Mar. 16, 1999

[54] INTRAVASCULAR METHOD AND SYSTEM FOR TREATING ARRHYTHMIA

[75] Inventors: Ruey Sung, Hillsborough; Gene Samson, Fremont, both of Calif.

[73] Assignee: Cardima, Inc., Fremont, Calif.

[ * ] Notice: The term of this patent shall not extend beyond the expiration date of Pat. No. 5,645,082.

[21] Appl. No.: 667,394

[22] Filed: Jun. 21, 1996

Related U.S. Application Data

[60] Division of Ser. No. 188,384, Jan. 27, 1994, Pat. No. 5,645,082, which is a continuation-in-part of Ser. No. 10,818, Jan. 29, 1993, abandoned, and a continuation-in-part of Ser. No. 43,449, Apr. 5, 1993, abandoned, and a continuation-in-part of Ser. No. 57,294, May 5, 1993, abandoned.

[51] Int. Cl.$^6$ ................................................ A61B 19/00
[52] U.S. Cl. .................................... 128/898; 606/195
[58] Field of Search ............................... 128/897–899, 128/634; 606/195, 200; 604/60; 600/342

[56] References Cited

U.S. PATENT DOCUMENTS

| | | | |
|---|---|---|---|
| Re. 33,925 | 5/1992 | Bales et al. ........................ 606/48 |
| 0,452,220 | 5/1981 | Gunning ............................. 607/116 |
| 4,271,847 | 6/1981 | Stokes ............................... 607/122 |
| 4,332,259 | 6/1982 | McCorkle, Jr. .................... 128/786 |
| 4,402,330 | 9/1983 | Lindemans ......................... 607/122 |
| 4,437,474 | 3/1984 | Peers-Trevarton ................. 607/119 |
| 4,449,528 | 5/1984 | Auth et al. ...................... 128/303.1 |
| 4,458,677 | 7/1984 | McCorkle, Jr. .................... 128/786 |
| 4,481,953 | 11/1984 | Gold et al. ....................... 128/642 |
| 4,559,951 | 12/1985 | Dahl et al. ....................... 128/642 |
| 4,690,155 | 9/1987 | Hess . |
| 4,777,955 | 10/1988 | Brayton et al. . |
| 4,785,815 | 11/1988 | Cohen et al. ..................... 128/642 |
| 4,840,186 | 6/1989 | Lekholm et al. .................. 128/784 |
| 4,867,173 | 9/1989 | Leoni ................................ 128/772 |
| 4,869,248 | 9/1989 | Narula ........................... 128/303.13 |
| 4,945,912 | 8/1990 | Langberg .......................... 128/642 |
| 4,955,382 | 9/1990 | Franz et al. ...................... 128/642 |
| 4,957,110 | 9/1990 | Vogel et al. . |
| 4,966,597 | 10/1990 | Cosman ............................. 606/50 |
| 4,979,510 | 12/1990 | Franz et al. ...................... 128/642 |
| 5,029,585 | 7/1991 | Lieber et al. ..................... 128/642 |
| 5,044,375 | 9/1991 | Bach, Jr. et al. ................. 128/786 |
| 5,056,517 | 10/1991 | Fenici et al. ..................... 128/419 |
| 5,083,565 | 1/1992 | Parins ............................... 128/642 |
| 5,095,916 | 3/1992 | Smits . |
| 5,095,917 | 3/1992 | Vancaillie ......................... 128/831 |
| 5,099,838 | 3/1992 | Bardy . |
| 5,104,393 | 4/1992 | Isner et al. ......................... 606/15 |
| 5,122,136 | 6/1992 | Guglielmi et al. .................. 606/32 |
| 5,125,896 | 6/1992 | Hojeibane . |
| 5,133,731 | 7/1992 | Butler et al. ...................... 606/191 |
| 5,140,987 | 8/1992 | Schuger et al. . |
| 5,163,445 | 11/1992 | Christian et al. .................. 607/116 |
| 5,165,403 | 11/1992 | Mehra . |
| 5,170,802 | 12/1992 | Mehra . |
| 5,172,699 | 12/1992 | Svenson et al. ................... 128/705 |
| 5,174,288 | 12/1992 | Bardy et al. ..................... 128/419 D |
| 5,184,621 | 2/1993 | Vogel et al. ....................... 128/642 |
| 5,193,546 | 3/1993 | Vogel et al. . |
| 5,193,550 | 3/1993 | Duffin ............................... 128/697 |
| 5,215,103 | 6/1993 | Desai ................................ 128/784 |
| 5,222,970 | 6/1993 | Reeves .............................. 606/195 |
| 5,330,522 | 7/1994 | Kreyenhagen ..................... 607/122 |
| 5,334,210 | 8/1994 | Gianturco ......................... 606/151 |
| 5,364,352 | 11/1994 | Cimino et al. ...................... 604/95 |
| 5,645,082 | 7/1997 | Sung et al. ......................... 128/897 |

FOREIGN PATENT DOCUMENTS

| | | | |
|---|---|---|---|
| 0293499 | 7/1988 | European Pat. Off. ........... 607/116 |
| 0 369 044 | 5/1990 | European Pat. Off. . |
| 1813232 | 6/1969 | Germany .......................... 607/116 |
| 2605590 | 8/1977 | Germany .......................... 607/123 |
| 3718139C1 | 12/1988 | Germany . |
| WO 80/02801 | 12/1989 | WIPO . |
| WO 90/03151 | 4/1990 | WIPO . |
| WO 92/21278 | 12/1992 | WIPO . |
| WO 93/08755 | 5/1993 | WIPO . |
| WO 93/08756 | 5/1993 | WIPO . |
| WO 93/08757 | 5/1993 | WIPO . |
| WO 93/08869 | 5/1993 | WIPO . |
| WO 94/06349 | 3/1994 | WIPO . |

OTHER PUBLICATIONS

Lawrence T. Weston, M.D., et al., "A Prototype Coronary Electrode Catheter for Intracoronary Electrogram Recording," *The American Journal of Cardiology*, vol. 70, Dec. 1, 1992, pp. 1492 and 1493.

Inoue, et al., "Intracoronary Ethyl Alcohol or Phenol Injection Ablates Aconitine–Induced Ventricular Tachycardia in Dogs," *J. Am. Coll. Cardiol.*, vol. 10, No. 6, Dec. 1987, pp. 1342–1349.

Szabo, et al., "Localization of Accessory Pathways in the Wolff–Parkinson–White Syndrome," *Pace*, vol. 12, Oct. 1989, pp.1691–1705.

(List continued on next page.)

*Primary Examiner*—John P. Lacyk
*Attorney, Agent, or Firm*—Heller Ehram White & McAuliffe

[57] ABSTRACT

A method and system for treating a patient's heart exhibiting arrhythmia by first detecting electrical activity within the patient's heart to determine the location of the arrhythmogenic site or conductive pathway causing the arrhythmia and then creating on infarct within the region of the patient's heart where the arrhythmogenic site or the conductive pathway causing the arrhythmia is located by delivering an occluding element to a coronary artery which delivers oxygenated blood to said region of the patient's heart. In one presently preferred embodiment the occluding element is a flaccid or limp coil which when disposed in a coronary arterial passageway forms a randomly shaped, intertwined mass which quickly forms thrombus within the coronary artery to block the passage of oxygenated blood therethrough. The flaccid coil may be delivered through an inner lumen of a catheter which has a distal portion extending within the coronary artery.

2 Claims, 7 Drawing Sheets

OTHER PUBLICATIONS

Swartz, M.D., et al., "Endocardial Atrial Catheter Ablation of Accessory Pathways After Intravascular Localization," NASPE Abstracts, *Pace*, vol. 13, Apr. 1990, p. 527, Abstract 126.

Fisher, et al., "Nonsurgical Electrical Ablation of Tachycardias: Importance of Prior in Vitro Testing of Catheter Leads," *Pace*, (1984) 7:74–81.

Brugada, et al., "Termination of Tachycardias by Interrupting Blood Flow to the Arrhythmogenic Area," *Am. J. Cardiology* (1988) 62:387–392.

Melvin M. Scheinman, M.D., "Catheter Techniques for Ablation of Supraventricular Tachycardia," *The New England Journal of Medicine*, Feb. 16, 1989, pp. 460–461.

Michael Haissaguere, M.D., et al., "Closed–Chest Ablation of Retrograde Conduction in Patients with Atrioventricular Nodal Rentrant Tachycardia," *The New England Journal of Medicine*, Feb. 16, 1989, pp. 426–433.

Repetto, et al., Transcoronary Epicardial Mapping of Accessory Pathways. Implications for Ablation Techniques. 10th Int'l. Cong., "The New Frontiers of Arrhythmias." Marilleva, Italy. Jan. 25–Feb. 1, 1992. pp. 475–480.

Lesh, M.D., et al., Mapping in the Right Coronary Artery as an Aid to Radiofrequency Ablation of Right–Sided Accessory Pathways. NASPE Abstracts. *Pace*, vol. 14, Apr. 1991, Part II, p. 671, Abstract 213.

DePaola, et al., "Transcoronary Chemical Ablation of Ventricular Tachycardia in Chronic Chagasic Myocarditis," *J. Am. Coll. Cardiol.*, vol. 20, No. 2, Aug. 1992:480–482.

Alden H. Harken, "Surgical Treatment of Cardiac Arrhythmias", *Scientific American*, Jul. 1993, pp. 68–74.

Hashimoto, et al., "Significance of S–T Segment Elevations in Acute Myocardial Ishemia," *The American Journal of Cardiology*, vol. 37, Mar. 31, 1976, pp. 493–500.

Walter, et al., Europ. Surg. Res. 3:130–138 (1971).

Brugada, et al., "Transcordary Chemical Ablation of Ventricular Tachycardia," *Circulation* (1989) 79:475–482.

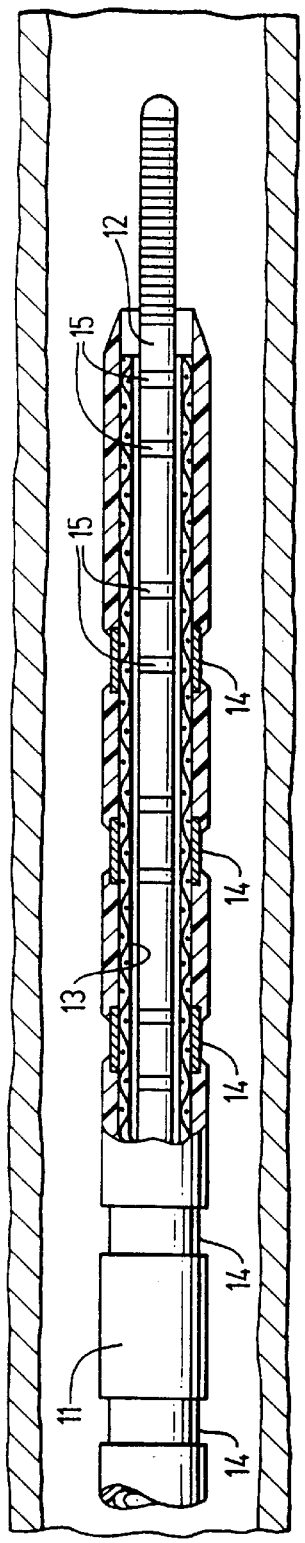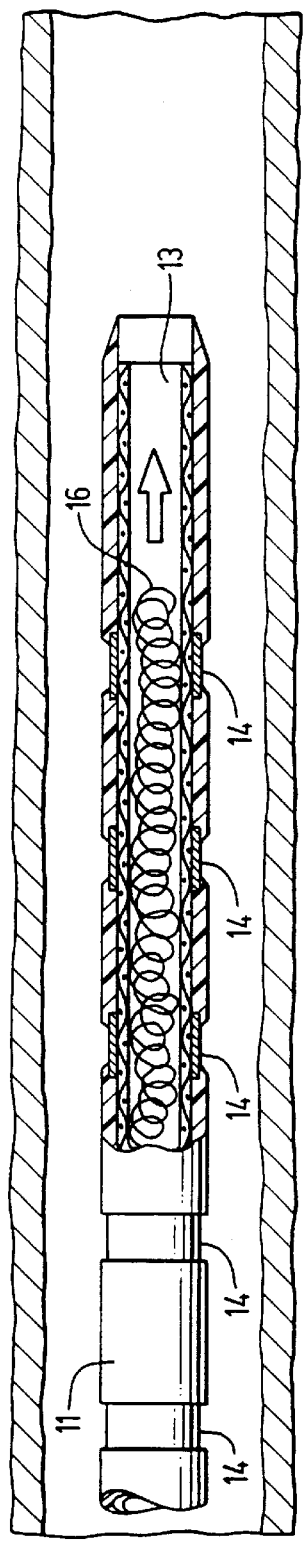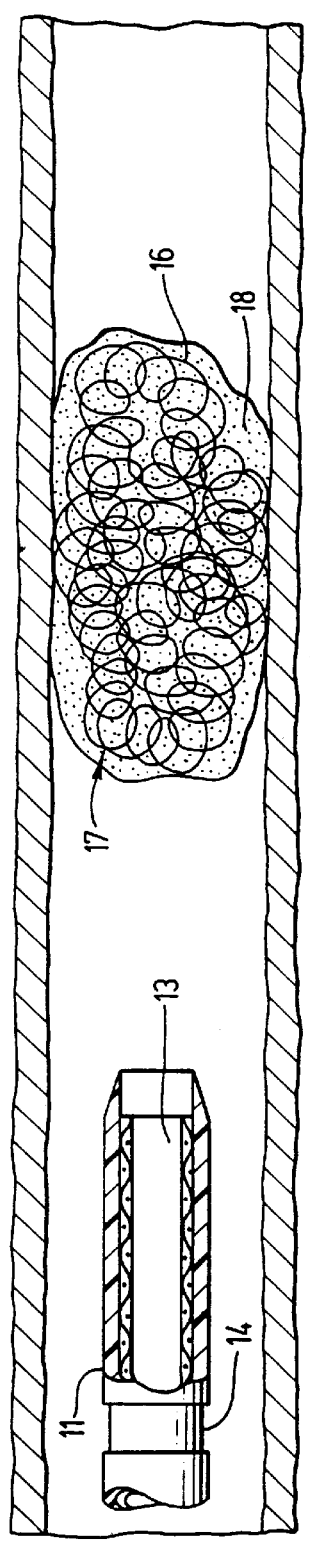

INTRAVASCULAR METHOD AND SYSTEM FOR TREATING ARRHYTHMIA

RELATED APPLICATIONS

This is a divisional application of application Ser. No. 08/188,384 which was filed on Jan. 27, 1994 now U.S. Pat. No. 5,645,082; which is a continuation-in-part of application Ser. No. 08/010,818, filed on Jan. 29, 1993 now abandonded; and a continuation-in-part of application Ser. No. 08/043,449, filed on Apr. 5, 1993 now abandonded; and a continuation-in-part of application Ser. No. 08/057,294, filed on May 5, 1993 now abandonded.

BACKGROUND OF THE INVENTION

This invention generally relates to the treatment of arrhythmia and particularly an intravascular method and system for treating arrhythmia.

Prior methods for treating a patient's arrhythmia include the use of antiarrhythmic drugs such as sodium and calcium channel blockers or drugs which reduce the Beta-adrenergic activity. Other methods include the surgically sectioning the origin of the signals causing the arrhythmia or the conducting pathway for such signals. More frequently, however, in order to terminate an arrhythmia the arrhythmogenic site which causes the arrhythmia or conductive pathways which propagate aberrant signals are destroyed by heat, e.g. applying a laser beam or radio frequency (RF) energy to a desired location on the patient's endocardium. A major problem of ablating the origin of the signals or a conductive pathway is to accurately determine the location of the site so that an excessive amount of good tissue is not destroyed adjacent the site.

For example, the average arrthythmogenic site consists of about 1.4 $cm^2$ of endocardial tissue, whereas a re-entrant site might be much larger. RF ablation techniques produce lesions about 0.5 $cm^2$ in diameter, so a number of lesions might be generated in order to completely abiate the area of interest, It the site is not accurately mapped, much of the good tissue surrounding the site will be unnecessarily destroyed.

Other methods to terminate arrhythmia have been tried but they have not been used clinically to any great extent for a variety of reasons. For example, ethanol may be injected into a branch of a coronary artery which feeds an arrhythmogenic region of the patient's heart or a conductive pathway therein to occlude the arterial passage and create a controlled infarct at the arrhythmogenic site or the conductive pathway to terminate the arrhythmia. However, due to reflux of the ethanol, it is not always possible to control the region of cytotoxic activity within the heart. Additionally, over time, it has been found that the occluded arterial passageway frequently is subject to recanalization which can allow the arrhythmia to return.

What has been needed is an effective method and system for permanently occluding a portion of a patient's coronary artery which feeds the tissue of a patient's heart causing the arrhythmia, such as an arrhythmogenic or re-entrant site or a conductive pathway, in order to the terminate an arrhythmia.

SUMMARY OF THE INVENTION

This invention is directed to a method and system for treating a patient's heart exhibiting arrhythmia by effectively occluding an arterial passageway which feeds oxygenated blood to heart tissue causing thee arrhythmia and which preferably includes the intravascular detection of electrical activity or signals within a patient's heart causing the arrhythmia.

In accordance with one aspect of the invention, the tissue causing the arrhythmia such as an arrhythmogenic or re entry site or a conductive pathway, is first located within a patient's heart, preferably intravascularly, and then an occluding element is advanced through the patient's coronary arterial system to a small arterial vessel where the occluding element is deposited to block the flow of oxygenated blood therethrough. The ischemic conditions created by such blockage distal to the occluding element ultimately leads to an infarct which terminates the arrhythmia. The occluding element of the invention remains in the coronary arterial passageway, so there is little tendency for recanalization to occur which might lead to the recurrence of the arrhythmia.

In one presently preferred embodiment of the invention, the occluding member is an open-bodied element such as a flexible helical coil or a braided tubular element which, when deposited in a small coronary arterial passageway, will promptly form thrombus and thereby occlude the arterial passageway. Preferably, the thrombus forming element is limp or flaccid so that when introduced into the arterial passageway it will form a randomly shaped, intertwined mass in which thrombus quickly forms to occlude the arterial passageway. Other means for occluding the arterial passageway include expandable occluding elements such as an inflatable balloon or an expandable mechanical element which blocks fluid flow through the passageway. The occluding means is preferably delivered to the desired location within the arterial passageway of the patient's heart by an intravascular catheter which has an inner lumen extending therein to a discharge port in the distal end of the catheter.

One presently preferred embodiment of the invention is an exceptionally flexible, ultrasoft vaso-occlusive or embolism device which is made of a radiopaque material which may be braided or coiled to form a long, thin threadlike device having little rigidity or column strength. The diameter of the device may be less than about 0.010 inches (0.25 mm), preferably less than about 0.0075 inches (0.19 mm) in diameter. The wire making up the device is typically of a diameter less than about 0.002 (0.05 mm) inches. The device is sufficiently flexible and small that it may be hydraulically delivered to a site within a coronary artery of a human heart using a catheter. The device is so light that it typically cannot be pushed from the catheter in the way that coils are often introduced into vascular site. Because of their flexibility and size, there is little opportunity for friction to develop with the catheter lumen.

The occluding device typically assumes a loose, random, initeltwined mass after being ejected from the catheter tip at the selected arterial site. The device, whether coil or braid, may be used in conjunction with larger coils or braids to achieve a denser occlusion.

This embodiment also includes first introducing a vaso-occlusive coil having a larger diameter to the vascular site desired by the attending physician, followed by the introduction of the flaccid coil of this embodiment so as to fill the interstices left by the larger coil and thereby form a denser occlusion. The coils may also be introduced by themselves, if so desired.

In another presently preferred embodiment, an elongated intravascular catheter used for delivering the occluding element has a plurality of sensing electrodes on the distal section thereof. After the occluding element is delivered into the arterial passageway through the inner lumen of the catheter, the sensing electrodes on the distal section of the catheter may be used to monitor tie electrical activity from within the arterial passageway to determine whether the arrhythmia has been effectively terminated. If it is determined that the arrhythmia has not been completely terminated by injecting a first occluding coil, other step may be taken such as delivering a second occluding element such as a coil through the inner lumen of the catheter to the blockage site to further occlude the arterial passageway to ensure the complete termination of the arrhythmia.

Once the arrhythmia has been terminated in accordance with the present invention, there is little likelihood that recanalization of the arterial passageway will occur and that the arrhythmia will reappear.

The preferred method to detect electrical activity within the patient's heart tissue causing arrhythmia is to position one or more elongated intravascular devices having sensing electrode on the distal section thereof within coronary arteries and/or cardiac veins of patient's heart. A suitable intravascular device has an elongated shaft with a proximal section and a distal section which is configured to be considerably more flexible than the proximal section and to be advanceable through a patient's tortuous coronary anatomy. The distal section has a plurality of electrodes spaced along a length of the distal section. Preferably, up to 20 or more bipolar electrode pairs may be provided along the distal section of the shaft. The sensing electrodes are electrically connected to electrical conductors which extend from the electrode to which they are connected to the proximal end of the shaft. In a presently preferred embodiment, the shaft of the intravascular sensing device is formed of a plurality of insulated electrical conductors which are braided of woven into an elongated tubular member, although not all of the strands which make up the braided or woven tubular member need be electrical conductors. Underneath each sensing electrode, the insulation on an individual conductor is removed to expose the bare conductor so that an electrical connection can be made between the electrode and the conductor. The electrical connection should be secured by suitable means such as conductive solder or brazing material. Moreover, the electrodes should also be secured to the underlying tubular member by other suitable means such as an adhesive to ensure that appropriate electrical contact with the exposed conductors is maintained even though there is a brazed or soldered electrical connection.

One form of a suitable elongated intravascular sensing device is a guidewire. The distal section of the guidewire having a plurality of sensing electrodes has a flexible tip coil which is distal to the length on which the electrodes are mounted and which is disposed about the distal extremity of a core member which extends through the interior of the shaft. The distal end of the core member may be manually shapable by the physician to facilitate steering the guidewire when it is being advanced within the patient's coronary anatomy by torquing the proximal end which extends outside of the patient. A smooth rounded tip is provided at the distal end of the coil to avoid damage, to the patient's vasculature when being advanced therethrough. A safety or shaping ribbon may extend from the distal end of the core member to the rounded tip in conventional guldewire fashion, commonly called a "floppy tip", to allow the distal portion to be manually shaped and also to prevent the loss of the distal tip of the guidewire within the patient's coronary vasculature.

The intravascular sensing device may also be in the form of a catheter which has proximal and distal sections with the distal section being more flexible that the proximal section and having a plurality of electrodes as in the guidewire form. In addition, the catheter has an elongated inner lumen extending from the proximal end to a discharge or guidewire port in the distal end of the device. The distal end of the catheter having the discharge port may be provided with a soft tip to minimize traumatic engagement with a blood vessel wall when being advanced therein. The catheter form allows an occluding element to be passed through the inner lumen into the arterial passageway and the sensing electrodes on the distal section thereof allows electrical activity to be monitored in order to determine the effectiveness of the arterial blockage and particularly whether the arrhythmia has been terminated. The inner lumen of the catheter may be configured to facilitate the slidable disposition of a conventional guidewire or a guidewire version of the sensing device of the invention such as described above.

The use of a plurality of elongated intravascular devices is preferred so that they can be advanced into separate blood vessels of the patient's heart to detect electrical activity in a plurality of intravascular locations, thereby providing more comprehensive or global mapping of the patient's heart and a more accurate location of tissue causing an arrhythmia. The positions of the intravascular sensing devices may be adjusted within the individual blood vessels to optimize the reception of the electrical activity to provide a greater degree of accuracy in detecting the ectopic foci.

The use of intravascular sensing devices to locate the tissue causing the arrhythmia simplifies the treatment procedures and reduces the overall time for the procedure. If the sensing device is a catheter, the occluding element can be quickly advanced through the inner lumen thereof. It the sensing device is a guidewire, a catheter with an inner lumen may be quickly advanced over the in-place guidewire, the guidewire removed and an occluding element advanced through the inner lumen of the catheter.

These and other advantages will become more apparent from the following detailed description of the invention and the accompanying exemplary drawings.

BRIEF DESCRIPTION OF THE DRAWINGS

FIG. 1 is a longitudinal cross-sectional view of catheter-guidewire assembly for detecting electrical signals within a coronary artery.

FIG. 2 is a longitudinal cross-sectional view of the catheter shown in FIG. 1 with the guidewire removed and a mass of occluding coil being hydraulically propelled along the inner lumen of the catheter.

FIG. 3 is a longitudinal cross-sectional view of the distal portion of the catheter shown in FIG. 1 with the mass of coil deposited within the arterial passageway an thrombus formed in the mass occluding the passageway of the coronary artery.

DETAILED DESCRIPTION OF THE INVENTION

Figure 4:
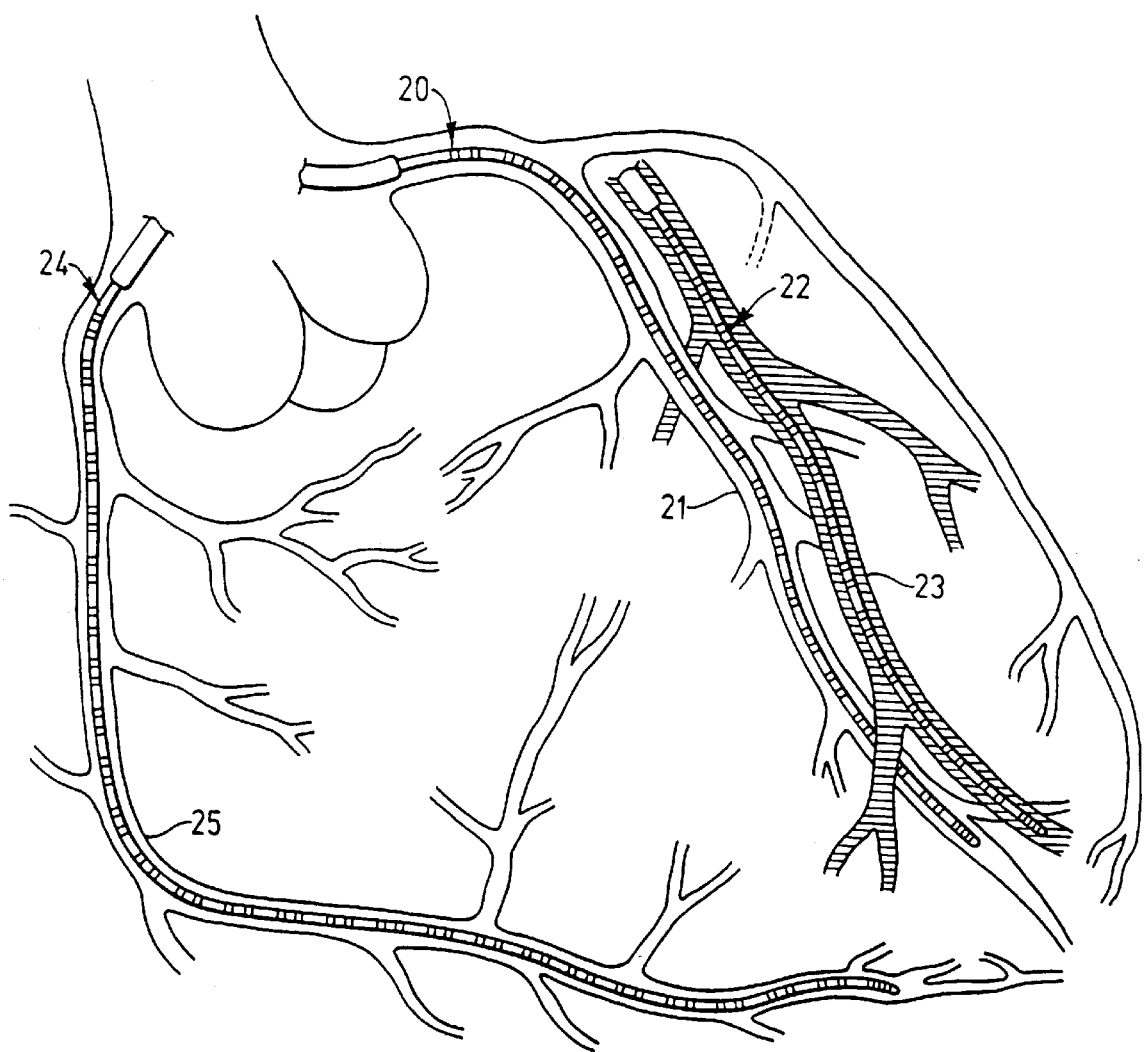
FIG. 4 is an anterior view of coronary arteries and cardiac veins of a human heart with portions of the right coronary artery, the anterior interventricular branch of the left coronary artery and the great cardiac vein being in section to illustrate intravascular devices disposed therein.
Figure 5:
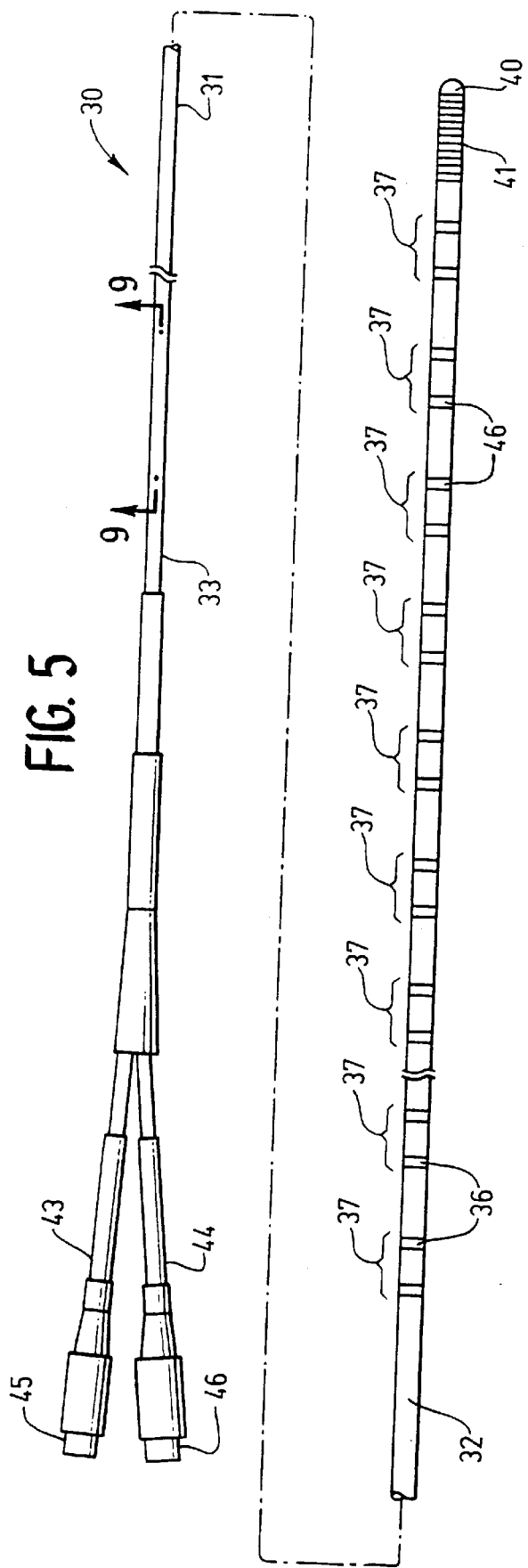
FIG. 5 is an elevational view of a guidewire suitable for detecting electrical activity.

FIGS. 1–3 illustrate one presently preferred method of the invention wherein electrical activity of a patient is detected from within a coronary artery 10 of the patient's heart to determine the location of tissue causing arrhythmia and then occluding the coronary artery which directs oxygenated blood to such tissue to create an infarct therein and thereby terminate the arrythmia. As is shown in FIG. 1, an intravascular catheter 11 is disposed within coronary artery 10 and an intravascular guidewire 12 is slidably disposed within inner lumen 13 of catheter 11. Catheter 11 has a plurality of sensing electrodes 14 on the distal section thereof and guidewire 12 has a plurality of sensing electrodes 15 on the distal portion thereof for detecting electrical activity so that tissue causing the arrhythmia can be located within the patient's heart. When the tissue causing the arrhythmia is located, the guidewire 12 is withdrawn from the inner lumen 13 of the catheter 11 and an elongated flaccid coil 16 is hydraulically delivered within a bolus of suitable liquid, such a saline solution, through the inner lumen 13, as illustrated in FIG. 2. When the coil 16 is deposited into the passageway of the coronary artery 10, it forms a randomly shaped intertwined mass 17. Thrombus 18 a quickly forms within the interstices of the coil mass to effectively occlude the arterial passageway.

As shown in FIG. 4, electrical activity of the patient's heart may be detected by a plurality of elongated intravascular sensing devices, with one sensing device 20 being disposed within the anterior interventricular branch of the left coronary artery 21, a second sensing device 22 in the great cardiac vein 23 and a third sensing device 24 in the right coronary artery 25. As shown, the intravascular sensing devices are guidewires.

Figure 6:
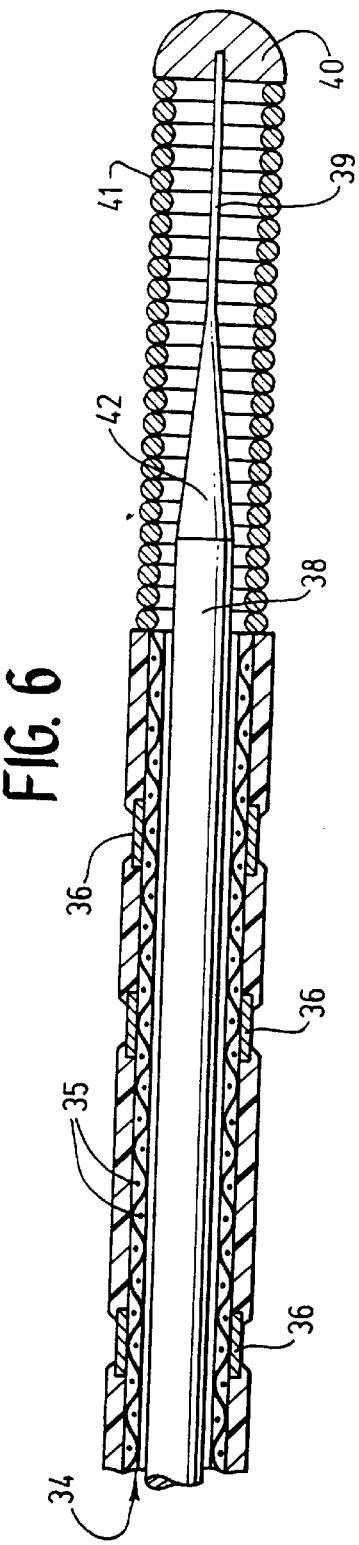
FIG. 6 is an enlarged longitudinal cross-sectional view of a distal portion of the guldewire shown in FIG. 5.
Figure 7:
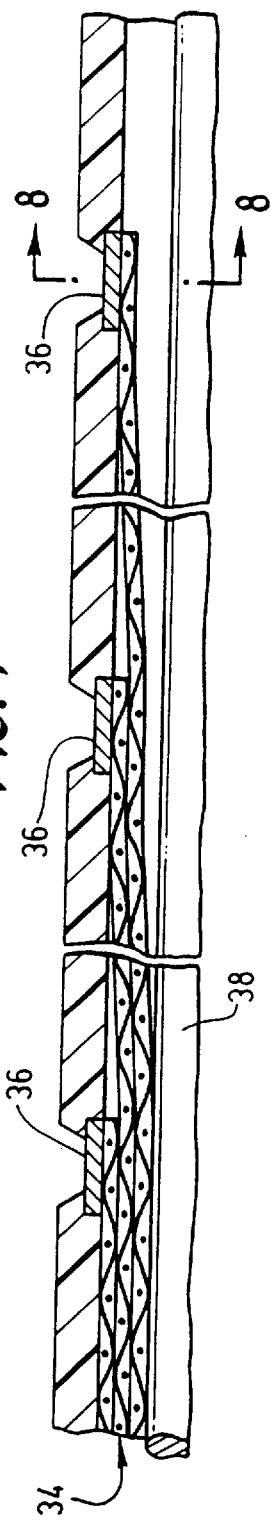
FIG. 7 is an enlarged longitudinal cross-sectional view of the distal portion of a guidewire similar to the one shown in FIG. 6 but having a shaft formed of a plurality of braided layers.
Figure 9:
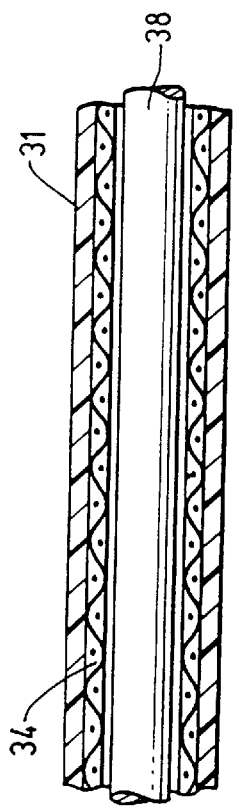
FIG. 9 is a longitudinal cross-sectional view of an intermediate portion of the guidewire shown in FIG. 5 taken along the lines 9—9.
Figure 8:
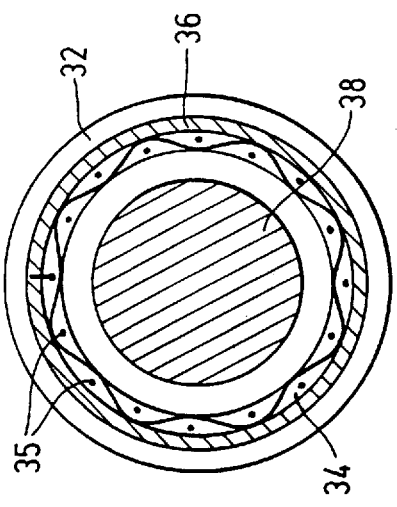
FIG. 8 is a transverse cross-sectional view of the distal portion of the guidewire shown in FIG. 7 taken along the lines 8—8.

Reference is made to FIGS. 5–9 which schematically illustrate in greater detail an elongated intravascular sensing device useful in the present invention which is in the form of a guidewire 30 which includes shaft 31 with a distal portion 32 and a proximal portion 33. The shaft 31 is formed of a tubular member 34 formed of a plurality of braided or woven electrical conductors 36. While it is preferable that the conductors 35 be interwoven into the tubular member 34, they may be twisted or wound about a mandrel or the core member 38. In the latter case the inner and outer layers of conductors would be laid out nationally but the conductors of one layer would be laid in the opposite direction to that of the conductors in the other layer. Usually, the wound or twisted conductors arc secured together by suitable adhesive which makes the shaft relatively stiff, whereas with the interwoven conductors there is sufficient interlocking of the conductors that adhesives are not usually needed with the result of a more flexible shaft 31. The distal section 32 of the shaft 31 is provided with a plurality of electrodes 36 which are preferably arranged as pairs 37 to facilitate a bipolar or multipolar mode of operation. A core member 38 is disposed within the inner lumen of the braided tubular member 34 and extends beyond the distal end thereof. The distal end 39 of the care member 38 is preferably flattened, as shown in FIG. 6, and extends and is joined to a smooth rounded distal tip 40 which is formed when a distal coil 41, which is disposed about the distal end of the core member, is secured thereto by soldering, brazing, welding or a body of adhesive and the like. The core member 38 may be provided with one or more tapers 42 as with conventional guidewires. The proximal portion 33 of the shaft 31 has two extensions 43 and 44 which have multi-pin connectors 35 and 46 on the proximal ends thereof with each of the electrical conductors 45 being electrically connected to a separate pin.

Figure 10:
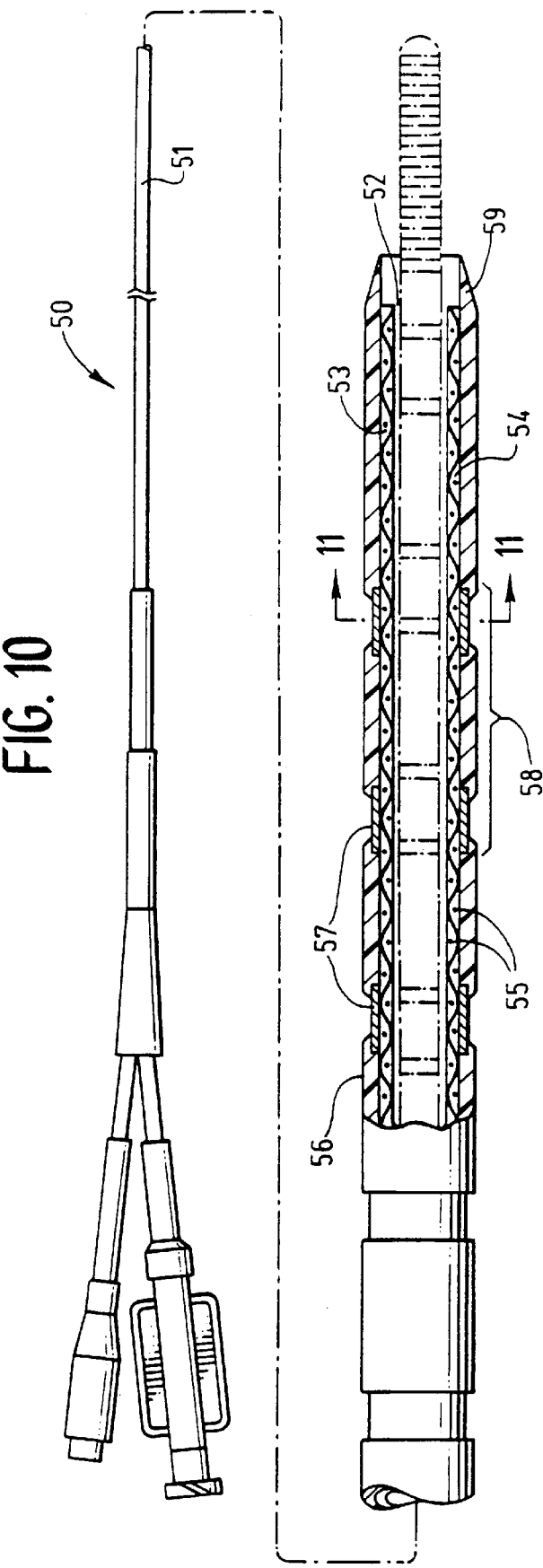
FIG. 10 is an elevational view, partially in section of a catheter suitable for detecting electrical activity.
Figure 11:
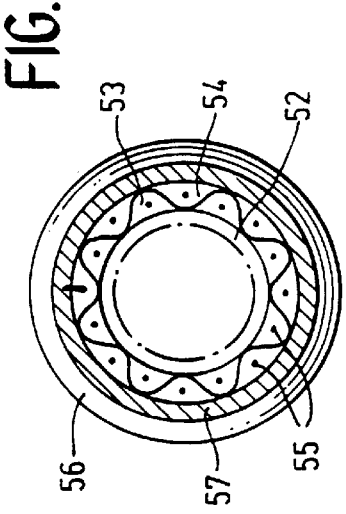
FIG. 11 is a transverse cross-sectional view of the catheter of FIG. 10 taken along the lines 11—11.

Details of the catheter form of the sensing device are best illustrated in FIGS. 10 and 11. In this embodiment, catheter 50 has an elongated shaft 51 with an inner lumen 62 defined by an inner tubular element or lining which is preferably formed of lubricous material such as fluoropolymers, e.g. Teflon® and polysulfones and hydrophilic polymers such as polyvinylpyrrolidone, polyethylene oxide and acrylate-based polymers. A tubular member 53 is disposed about tubular lining and is formed of at least one braided layer 54 comprising a plurality of the strands 55 which are insulated electrical conductors electrically connected to electrodes 57 preferably arranged in pairs 58 to facilitate bipolar mode operation. While not shown in the drawing, a plurality of braided layers may be desireable with more than eight electrode pairs 58. Some of the strands 55 in each of the layers may be formed of nonconducting materials such as nylon. An outer jacket 56 extends the length of the shaft 51 and the portion of the jacket extending beyond the distal end of the braided tubular member 52 is tapered to provide a nontraumatic flexible distal tip 59. As in the previously described embodiments, the outer jacket 56 overlaps the edges of the electrodes 57 to avoid exposing a sharp metal edge when advancing the catheter through a patient's blond vessel. A guidewire 60 (shown in phantom) is slidably disposed within the inner lumen 52.

The catheter 50 may be used to direct diagnostic or therapeutic fluids to distal locations within a patients coronary vasculature. For example, fluids containing cardioplegic materials such as iced saline, solutions of KCl, lidocaine, procaineamide hydrochloride and the like can be delivered to a region of the patient's heart which is believed to contain the tissue causing the arrhythmia. If the arrhythmia stops upon the delivery of the cardioplegic agent through a coronary artery feeding the region of the patient's heart, then the operator is assured that the artery through which the agent is delivered feeds the tissue causing the arrhythmia. The intravascular catheter 48 may be utilized in conjunction with a conventional guidewire or with an intravascular device with a plurality of electrodes an n distal portion thereof such as described above.

When using an approach to the patient's heart through the femoral artery or femoral vein, it is frequently helpful to utilize one or more guiding catheters (as shown, in FIG. 4) to guide the intravascular sensing devices of the invention to the coronary artery ostium or the coronary sinus ostium. Such guiding catheters frequently have specially shaped distal tips to facilitating the seating thereof within the desired ostium. The use of guiding catheter eliminates the need to direct the distal tip of a catheter or a guidewire of the invention into the desire ostium.

The electrodes on the distal portions of the sensing devices are typically gold bands with widths of about 0.5 mm. The distance between the electrodes of an electrode pair is typically about 1 mm and the distance between electrode pairs is typically about 7–8 mm.

The overall length of the intravascular devices of the invention depend upon the site of introduction into the patient's peripheral vasculature but may range from about 80 to about 300 cm, typically about 135 cm for delivery through the femoral artery or vein and about 90 cm for delivery through the brachiocephalic artery or internal jugular vein. The flexible distal portions of the intervascular sensing devices are about 10 to about 50 cm in length and are configured to be readily advanceable through a patient's coronary arteries or cardiac veins. The outer diameter of the catheter form of the sensing device should be less then about 0.055 inch (1.4 mm) and preferably about 0.035 inch (0.89 mm) and the inner lumen thereof is about 0.012 to about 0.022 inch (0.3–0.56 mm) in diameter to facilitate the reception and advancement of a guidewire therethrough. The distal portion of the guidewire is about 15 to about 40 cm in length and about 0.008 to about 0.022 inch (0.2–0.56 mm) in outer diameter to facilitate advancement through blood vessels having native diameters of less then 1 mm, frequently less than 0.75 mm. The distal coil on the guidewire is about 2 to about 10 cm in length and is formed of wire about 0.0003 to about 0.006 inch (0.0076–0.15 mm) in diameter. It is preferably formed of platinum to facilitate fluoroscopic observation thereof within the patient, but it may be formed in whole or in part with other material such as stainless steel, titanium, palladium, niobium, iridium, rhodium and alloys thereof.

To the extent not previously described, the materials of construction of the various guidewire and catheter parts may be formed of conventional materials. The electrical conductors may be electrical grade copper wire about 0.005 inch (0.127 mm) in diameter which are provided with a thin insulated jacket or coating of polylmide or other suitable insulator. The outer jacket may be a thermoplastic fluoropolymer such as THV which is available from 3M Corporation. The core wire of the guidewire many be formed of stainless steel or a superelastic NiTi type alloy the latter exhibiting a stable austenite phase at body temperature. Proximal and distal sections of the core member may he formed of different materials so as to provide a stronger proximal section for greater pushability and a more flexible distal section to facilitate passage through tortuous coronary anatomy. Manufacturing techniques used in making catheters and guidewires for angioplasty procedures may be used in the making of the intravascular devices of the invention.

Figure 12:
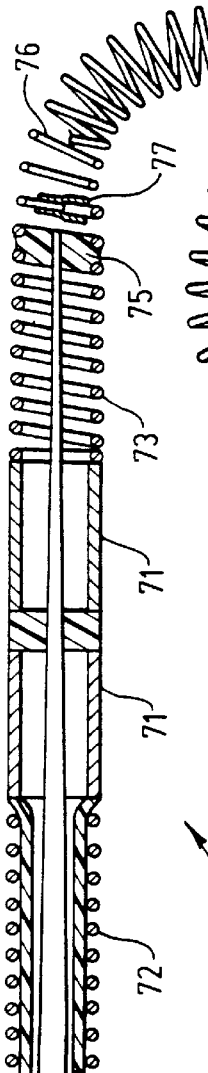
FIG. 12 is a longitudinal cross-sectional view of a guidewire having a releasable occluding element on its distal end.

An alternative embodiment of the invention in the form of a guidewire 70 is shown in FIG. 12 which has a single pair of electrodes 71 on distal section 72. A coil 73 is disposed about the distal portion of core member 74 distal to the distal electrode 71 and it is secured to the core member by a suitable means 75. Such securing may be effected by soldering, brazing, welding or suitable adhesive depending upon the materials from which the coil 73 and the core member 74 are made. The distal end of the guidewire 70 has a detachable vaso-occlusive coil 76 attached at the most distal end of the guidewire. The core member 74 is extended past the separator tip 77 and forms an electrical connection with vaso-occlusive coil 7 at the connection 75.

The intravascular device shown in FIG. 12 may be used in the following fashion. The guidewire 70 is advanced out of an intravascular catheter into a desired location within a coronary artery of the patient and the connection between the vaso-occlusive coil 76 and the core member 74 is severed by electrolytic activity so that the coil 76 is released from the guldewire. When released, the coil 86 forms a randomly shaped intertwined mass similar to that shown in FIG. 3. Thrombus quickly forms within the interstices of the coiled mass to occlude the arterial passageway. The sensing electrodes 71 on the distal section of the guidewire 20 may be used to monitor electrical activity to ensure that the arrhythmia has been terminated.

Figure 13:
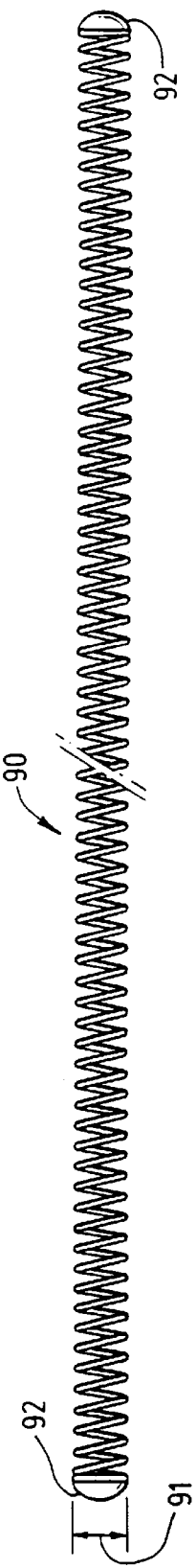
FIG. 13 is an elevational view of an occluding element suitable for use with the invention.

FIG. 13 shows a coil (90) suitable for use with this invention. It preferably has a diameter (91) of about 0.00075 to about 0.00225 inches, more preferably about 0.001 to about 0.002 inches. A separate end cap (92) or termination piece may be included at each end of the coil 90 to prevent the coil from catching on the interior of the catheter or a blood vessel. The end cap or termination piece (92) may be a separate piece or a fused portion of the coil 90 or a bit of a filled material such as an epoxy.

The coil 90 is typically produced as a single-layer coil with a minimum helical pitch, i.e. the windings are fairly closely packed. The outside diameter of the coil should be less than 0.010 inches, (0.25 mm) preferably between about 0.004 and 0.0095 inches (0.1–0.24 mm), and most preferably between 0.004 and 0.0075 inches (0.1–0.19 mm). The soft, flexible coil thus produced is cut to desired lengths after the formation thereof. The coil is especially suitable for the noted service when the device (coil, braid, or combination) deflects more than about 20° (preferably more than about 35°) under its own weight over the first centimeter of length when supported at a single end. The length of the coil may be between about 2 mm and about 120 cm, typically between about 30 cm and 120 cm.

Instead of the wire shown in FIG. 13, the coil 90 may be produced from a ribbon whose major axis is between about 0.001 and about 0.002 (0.025–0.05 mm) inches and whose minor axis is about 0.0005 and about 0.001 inches (0.013–0.025 mm). Coils produced from ribbons are often moderately stiffer than those produced from wire. Smaller diameter coils are often more readily produced.

The regularity of winding shown in FIG. 13 is not mandatory; the winidings may be Irregular or of varying pitch. The coil (90) shown in FIG. 13 (and the variations of the invention which are described below) may be produced from any of a number of different materials. The material should be radiopaque so that the coil and its position may be readily monitored within the human vasculature. Suitable materials include biocompatible metals, polymers, and alloys. for instance, biocompatible, radiopaque metals include silver, gold, palladium, platinum, tungsten, iridium, rhodium, Various stainless steels and alloys thereof. A particularly suitable alloy is 92% (by weight) platinum and 8% (by weight ) tungsten. The platinum-tungsten alloys desirably have a tensile strength of at least about 180 ksi (124 MPa) and, for a wire of a nominal 0.001" diameter, have a breaking load of 0.17 lb. with a minimum elongation of 2% measured at a speed of 1.0 in/min. Various biocompatible polymers including polyethylene, polyurethane, polypropylene, and the like are suitable for use in these devices, but, because of their lack of radiopacity, must usually be teamed with a radiopaque marker to allow proper positioning of the coil within the body. Similarly, other inorganic materials such as fibrous carbon are suitable and may be used in the invention.

Figure 14:
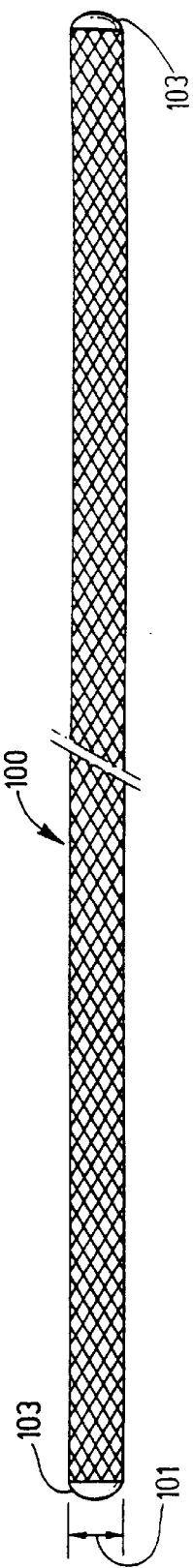
FIG. 14 is an elevational view of another occluding element suitable for use with the invention.

FIG. 14 shows a braided (or otherwise) woven vaso-occlusive device 100 suitable for use in the invention. The braided occlusive device 100 is tubular and produced by weaving fibers or wires over a mandrel much in the same way the coil of FIG. 13 was made. Woven braids of this size are not common but are made according to known techniques. The wire or fibers in this variation of the invention may be any of the radiopaque or polymeric materials noted above, and additionally the braid may be made of a combination of those materials either alone or in combination with other suitable polymeric or filamentary materials such as dacron, cotton, or other materials. Natural or synthetic polymer fibers such as dacron or cotton provide a ready substrate for clot formation in the interior region of a vessel. Often the radiopaque portion of the coil provides only a way to anchor the acyl onto the vessel wall at the site of release.

The FIG. 14 braid or woven device 100 is of a diameter 101 similar to the diameter of the device shown in FIG. 13. The braid may have a termination pieces 103 or end sections similar in constitution to the analogous portion shown in FIG. 11 above. The length of the braid may similarly be 2 mm to 120 cm.

Figure 15:
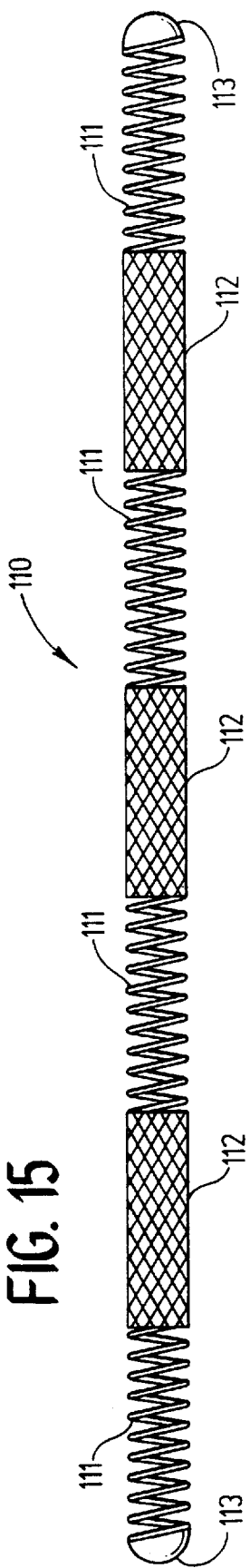
FIG. 15 is an elevational view of another occluding element suitable for use with the invention.

FIG. 15 shows a side view of a combination coil/braid vaso-occlusive device 110 according to the invention. This combination is a sequence of coils 111 and braids 112 similar in make-up and size as the devices shown in FIGS. 12 and 13. Lengths of various coils 111 and braids 112, each often 2 mm to 20 cm in length, are joined together at their respective ends to form the combination device. The overall length of the device 110, as with those above, may be 2 mm to 120 cm. The device 110 may also have caps or termination pieces (113) on the ends of the device.

Figure 16:
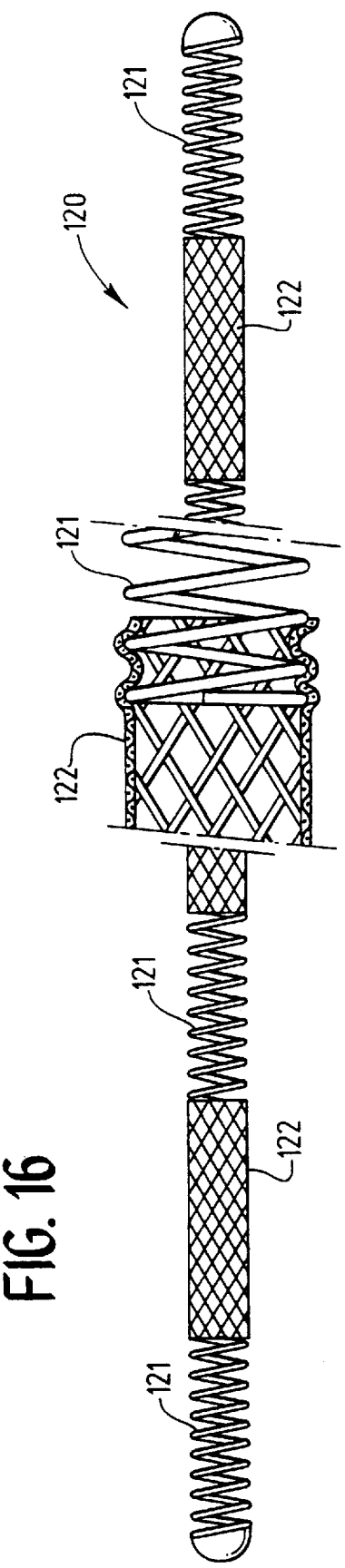
FIG. 16 is an elevational view of another occluding element suitable for use with the invention.

FIG. 16 shows another variation of a coil/braid combination 120. In this variation, however, as is shown by the cutaway insert, the substrate coil 121 is Identical to the coil shown in FIG. 11 herein. The braid 122 is woven on the exterior of the coil. In this instance, the braid is more desirably a fibrous material such as dacron or cotton. The braid may, however, be a radiopaque material such as the metals and alloys and polymers discussed above. The braid may be joined by welding, melting, or by adhesion to the underlying coil 121.

Each of the variations discussed above, when provided in the proper size range and materials, is an extremely soft and flexible device, whether the device by coil or braid. These devices exert little, if any, radial force on the blood vessels into which they are placed. The fluid-like properties of the coil within a carrier fluid enable it to conform to the complex geometry of certain fragile, abnormal blood vessels, and in so doing, minimize the risk of causing trauma to or perforation of those blood vessels. Such flow properties also enable coil placement in coronary vasculature currently unreachable by other occluding elements.

Vaso-occlusive coils and their method of introduction are discussed in detail In U.S. Pat. No. 5,122,136 (Gugliemi et al.). In cardiac occlusion, the length of the coil is fairly short to allow "microcontrol" of the occlusion of the small cardiac arteries and resultant control of the arrhythmia. The Gugliemi et al. patent is incorporated herein in its entirety by reference.

Alternative vaso-occlusive devices including tubular braids, as found in Ser. No. 07/965,973, and coils with or without fibrous attachments, such as found in Ser. No. 07/771,013 or 07/978,230, may simply be pushed through the catheter lumen using a guidewire. The aforesaid applications are incorporated herein in their entirety by reference.

The present invention has been described herein in terms of certain preferred embodiments but various modifications and improvements may be made to the present invention without departing from the scope thereof.

What is claim is:

1. A method for locating and treating an arrhythmogenic site in a patient's heart to terminate arrhythmia, comprising:

a) providing an elongated intravascular device having
      an elongated shaft with a proximal section and a distal section which is much shorter than the proximal section and which is configured to be advanced though a patient's coronary artery,
      a plurality of sensing electrodes longitudinally disposed along the distal section of the intravascular device,
      a plurality of electrical conductors which are connected to the sensing electrodes and which extend from said electrodes to which they are connected to a proximal section of the intravascular device,
      a releasable occluding member secured to the distal section;
   b) advancing the elongated intravascular device through the patient's vasculature until the distal section of the intravascular device is disposed at a desired location within the patient's coronary arterial system;
   c) locating the arrythmogenic site by detecting electrical activity of the patient's heart by means of the electrodes on the distal section of the intravascular device; and
   d) releasing the occluding member within an arterial passageway of the patient's coronary arterial system so as to form thrombus and thereby occlude the coronary artery leading to the arrhythmogenic site to thereby terminate the arrhythmia.

2. The method of claim 1 wherein the occluding member is a helical coil which is secured to the distal section of the intravascular device by means of a soldered joint and including the steps of disposing the intravascular device within the arterial passageway which is to be occluded and separating the occluding member from the intravascular device by electrolysis of the soldered joint between the intravascular device and the helical coil.

* * * * *